(12) United States Patent
Quetel et al.

(10) Patent No.: US 12,285,899 B2
(45) Date of Patent: Apr. 29, 2025

(54) MEANS OF STERILIZING THE STRETCHING MEANS OF A CONTAINER MOLDING DEVICE, AND CONTAINER MANUFACTURING INSTALLATION

(71) Applicant: SIDEL PARTICIPATIONS, Octeville-sur-Mer (FR)

(72) Inventors: François Quetel, Octeville-sur-Mer (FR); Benjamin Yger, Octeville-sur-Mer (FR); Sandy Letellier, Octeville-sur-Mer (FR)

(73) Assignee: SIDEL PARTICIPATIONS, Octeville-sur-Mer (FR)

( * ) Notice: Subject to any disclaimer, the term of this patent is extended or adjusted under 35 U.S.C. 154(b) by 0 days.

(21) Appl. No.: 17/684,349

(22) Filed: Mar. 1, 2022

(65) Prior Publication Data
US 2022/0324154 A1 Oct. 13, 2022

Related U.S. Application Data (62) Division of application No. 16/065,619, filed as application No. PCT/FR2016/053625 on Dec. 22, 2016, now Pat. No. 11,292,179.

(30) Foreign Application Priority Data

Dec. 22, 2015 (FR) ...................................... 1563052

(51) Int. Cl.
*B29C 49/06* (2006.01)
*A61L 2/20* (2006.01)
(Continued)

(52) U.S. Cl.
CPC .............. *B29C 49/06* (2013.01); *A61L 2/208* (2013.01); *B29C 49/006* (2022.05);
(Continued)

(58) Field of Classification Search
CPC .......................... B29C 49/06; B29C 49/42069
See application file for complete search history.

(56) References Cited

U.S. PATENT DOCUMENTS 5,399,302 A * 3/1995 Noguchi ................. B29C 49/70
264/412
6,562,281 B1 5/2003 Marchau et al.
(Continued)

FOREIGN PATENT DOCUMENTS

EP 2 094 312 9/2009
EP 2 292 406 3/2011
(Continued)

OTHER PUBLICATIONS

International Search Report, PCT/ FR2016/053625, dated Apr. 25, 2017.

*Primary Examiner* — Kevin Joyner
(74) *Attorney, Agent, or Firm* — Blake T. Hudson (57) ABSTRACT

The present invention relates to an installation for manufacturing containers made of thermoplastic material, having a sterilizing mode and a production mode. The installation comprising a molding machine, a transfer means, and a decontamination device. The molding machine is equipped with at least one molding device having stretching means, and the molding device is designed to manufacture by stretch blow molding said containers from preforms when the installation is in production mode. The transfer means conveys the manufactured containers between the molding machine and a second downstream machine when the installation is in production mode. The decontamination device introduces the sterilizing agent into at least one sterilizing preform during the sterilizing mode. The installation further comprises removal means that can be actuated in sterilizing (Continued)

mode to remove the hollow bodies from the transfer means upstream from the second machine.

18 Claims, 1 Drawing Sheet

(51) Int. Cl.
    *B29C 49/00*     (2006.01)
    *B29C 49/42*     (2006.01)
    *B29C 49/64*     (2006.01)
    *B29C 49/12*     (2006.01)
    *B29C 49/46*     (2006.01)
    *B29K 67/00*     (2006.01)
    *B29L 31/00*     (2006.01)
    *B65B 55/10*     (2006.01)

(52) U.S. Cl.
    CPC .. *B29C 49/42069* (2022.05); *B29C 49/42822* (2022.05); *B29C 49/6418* (2013.01); *A61L 2202/23* (2013.01); *B29C 49/12* (2013.01); *B29C 49/46* (2013.01); *B29K 2067/003* (2013.01); *B29L 2031/712* (2013.01); *B65B 55/10* (2013.01); *B65B 2210/06* (2013.01)

(56) References Cited

U.S. PATENT DOCUMENTS

| | | | |
|---|---|---|---|
| 7,806,680 B2 | 10/2010 | Adriansens et al. | |
| 7,867,440 B2 | 1/2011 | Quetel et al. | |
| 7,938,639 B2 | 5/2011 | Adriansens et al. | |
| 8,083,512 B2 | 12/2011 | Adriansens | |
| 8,092,757 B2 | 1/2012 | Adriansens et al. | |
| 8,517,710 B2 | 8/2013 | Duclos et al. | |
| 8,647,101 B2 | 2/2014 | Quetel et al. | |
| 2005/0118057 A1 | 6/2005 | Quetel et al. | |
| 2008/0260887 A1 | 10/2008 | Adriansens et al. | |
| 2009/0081326 A1 | 3/2009 | Adriansens et al. | |
| 2009/0317506 A1 | 12/2009 | Adriansens | |
| 2010/0047120 A1 | 2/2010 | Adriansens et al. | |
| 2011/0059197 A1 | 3/2011 | Duclos et al. | |
| 2011/0142731 A1* | 6/2011 | Beckmann | B67B 3/003 422/292 |
| 2011/0250307 A1 | 10/2011 | Quetel et al. | |
| 2016/0263269 A1* | 9/2016 | Hayakawa | B65B 55/10 |
| 2016/0325482 A1 | 11/2016 | Hayakawa et al. | |
| 2018/0186057 A1 | 7/2018 | Hayakawa | |

FOREIGN PATENT DOCUMENTS

| | | |
|---|---|---|
| EP | 2 772 447 | 9/2014 |
| FR | 2 915 127 | 10/2008 |
| FR | 2 940 964 | 7/2010 |
| JP | 2015171812 | 10/2015 |
| WO | WO 99/03667 | 1/1999 |
| WO | WO 03/084818 | 10/2003 |
| WO | WO 2006/136498 | 12/2006 |
| WO | WO 2006/136499 | 12/2006 |
| WO | 2015/125808 | 8/2015 |
| WO | 2016175237 | 11/2016 |

* cited by examiner

MEANS OF STERILIZING THE STRETCHING MEANS OF A CONTAINER MOLDING DEVICE, AND CONTAINER MANUFACTURING INSTALLATION

CROSS-REFERENCE TO RELATED APPLICATIONS

This application is Divisional Application of U.S. application Ser. No. 16/065,619 filed on Jun. 22, 2018 (now U.S. Pat. No. 11,292,179), which application is a 371 U.S. National Stage Application of PCT Application Serial Number PCT/FR2016/053625 filed on Dec. 22, 2016, the entire contents of each of which are hereby incorporated herein by reference.

This invention relates to a method of sterilizing the stretching means of a container molding device, as well as a container manufacturing installation.

This invention relates more particularly to a method for the sterilization of the stretching means of a container molding device equipping a manufacturing installation for containers made of thermoplastic material that are obtained by stretch blow molding from production preforms.

STATE OF THE ART

Such container molding devices are known from the state of the art, said molding devices equipping in particular a molding machine of an installation for the manufacture of containers.

In such a container manufacturing installation, implementing various measures for the purpose of checking and controlling the microbiological quality of the manufacturing environment as well as that of the containers is known.

Most notably, it is desired to eliminate all pathogens, such as germs, spores, bacteria, etc.

In fact, such pathogens are likely to affect the product that is packaged in the containers, particularly in the case of food products.

To do this, the measures are not aimed exclusively at the decontamination of the containers or that of the production preforms from which they are manufactured, but also the manufacturing installation itself.

The documents of the state of the art cited below, and to which reference will be made for further details, illustrate such measures by way of nonlimiting examples.

In particular, it is possible to distinguish, on the one hand, the measures that aim to destroy the pathogens, and, on the other hand, the measures that aim more generally to prevent the contamination of the containers by such pathogens.

The document FR-2,915,127 describes a container manufacturing installation having a protective enclosure that delimits a zone inside of which is provided a container molding machine of the blow-molding type that is supplied by means for transferring previously thermally-conditioned production preforms into an oven.

According to the teachings of this document, the installation has a system for blowing filtered air inside the enclosure particularly to establish an overpressure there so as to limit the risks of contamination of both the production preforms coming out of the oven and the manufactured containers.

The document FR-2,940,964 proposes improved means for the retracting of a transfer wheel acting between the output of the molding machine (blowing machine) and a filling machine so as to limit certain contamination risks.

This document teaches more particularly the contamination risks that are inherent with any human intervention (operators) in the immediate environment of the machines of a container manufacturing installation, for example for maintenance but generally speaking regardless of the purpose of the intervention.

The document WO-03/084818 describes, for example, a decontamination treatment by irradiation of the neck of production preforms by an ultraviolet (UV)-type radiation, before the introduction of said production preforms into the oven.

The document EP-2,094,312 describes, for example, a treatment by irradiation with an ultraviolet (UV) radiation that is implemented in a particular manner in an oven to decontaminate at least the outer surface of the production preform during thermal conditioning.

The documents WO-99/03667; WO-2006/136498 and WO 2006/136499 describe examples of decontamination treatment of the inner wall of a production preform by using a sterilizing agent, such as hydrogen peroxide.

Of course, the different examples of above-cited measures can be simultaneously implemented within the same installation to reduce drastically the risks of contamination.

A container manufacturing installation is also described and shown in FIG. 1 of the document EP-A1-2,292,406 to which reference will be made for a detailed description.

The invention relates more particularly to another of these measures that consists in performing a disinfection of the stretching means of each container molding device by using an alcohol-based solution.

During the manufacture of containers by stretch blow molding, the stretching means come into contact with the bottom of the production preform to stretch it axially. There is then a risk of contamination of the interior of the manufactured containers by pathogens that would be present on the stretching means.

A contamination of the interior of the production preform by the stretching means, generally consisting of a stretching (or elongating) rod, is even more critical when the decontamination of the interior of said preform has been performed upstream from the container molding machine.

Such a disinfection of the stretching means is performed before beginning the manufacture of containers, but this disinfection with alcohol does not, however, provide complete satisfaction.

Although alcohol has the advantage of being able to be eliminated by simple evaporation, alcohol also has the drawback of having only minimal effects with respect to certain pathogens.

In addition, the spraying of the stretching means with alcohol is generally performed by at least one operator. Now, the fact that an operator enters the interior of the installation to perform the disinfection of the stretching means also causes risks of contamination of the manufacturing environment.

As described in the above-cited document FR-2,915,127, a container manufacturing installation is generally delimited by an enclosure in an effort to be able to seal off the interior of the installation and to control the quality of the air therein.

The disinfection operation, requiring the presence of at least one operator for it, adds a new risk of contamination of the manufacturing environment by pathogens of which said operator would be a carrier.

Such risks have, for example, already been described particularly in the above-cited document FR 2,940,964, to which reference will advantageously be made for further details.

The document US20160325482, moreover, has described a blow-molding machine and a method of sterilizing this machine. The method described consists in filling the preform with a sterilizing liquid and in blowing air into this preform to distribute said sterilizing liquid in the forming machine by blowing. This makes it possible to sterilize the blow-molding machine without manual intervention. However, this presents in particular the drawback of running the risk of polluting the blow-molding machine that it is desired to sterilize by an amount of sterilizing agent that remains in the machine that is not compatible with the standards in force for the manufacture of containers containing food products.

The purpose of this invention is in particular to propose a new solution so as to perform an effective sterilization of the stretching means of a molding device used for the manufacture of containers made of thermoplastic material, particularly for food use.

GENERAL DESCRIPTION OF THE INVENTION

For this purpose, the invention proposes a method of sterilizing the stretching means of a container molding device equipping an installation for manufacturing containers made of thermoplastic material obtained by stretch blow molding from production preforms; said method for sterilizing the stretching means has at least the steps consisting in:
  introducing a determined amount of a sterilizing agent inside a sterilizing preform,
  during a so-called transformation step, transforming said sterilizing preform into a hollow body by stretch blow molding in said molding device.

According to the invention, said introduction of the sterilizing agent occurs in the vapor state in a sterilizing preform having a temperature that makes it possible to obtain a depositing by condensation of a uniform film of mist on an inner surface of said sterilizing preform, and the successive transformation into hollow bodies of at least two sterilizing preforms in the same molding device is initiated.

Such a method has the advantage in relation to the above-cited document US20160325482 that the amount of sterilizing agent introduced into the molding machine is much less. This makes it possible to be able much more quickly to bring the residual rate of sterilizing agent back to an acceptable level for the production of containers having a food use. Thus, this makes it possible to commence much more quickly the container production mode with production preforms. In fact, the amount of sterilizing agent deposited in the preforms for sterilization by condensation is extremely small, but sufficient to contribute to the sterilization of the stretching means. In addition, the fact of sterilizing the stretching means by the stretching of several successive sterilizing preforms makes it possible to distribute the sterilizing effect over several operations for transformation of the sterilizing preforms and thus to reduce further the amount of sterilizing agent entering the molding machine. Finally, the amount of sterilizing agent introduced into the molding machine is not proportionate with that implicit in the filling of the preforms with a liquid sterilizing agent.

The method of sterilizing the stretching means according to the invention also makes it possible to eliminate the alcohol disinfection of the stretching means performed manually by at least one operator, before the manufacture of containers in the installation, since it is the sterilizing agent contained in the sterilizing preform that acts to sterilize the stretching means when the latter penetrate the sterilizing preform.

Advantageously, the sterilization method according to the invention is implemented automatically in a container manufacturing installation having a molding machine equipped with at least one molding device provided with stretching means.

The presence of an operator inside the installation for a manual intervention is therefore no longer necessary; the sterilization method according to the invention thus makes it possible to eliminate completely the associated risks of contamination of the manufacturing environment.

As a result of the sterilization of the stretching means, the risks of contamination of the containers and most particularly the risks of contamination linked to the presence of pathogens on the stretching means of a molding device are even further reduced, and even eliminated.

According to an advantageous embodiment, the sterilizing agent contains hydrogen peroxide, the method comprising a step for activating the hydrogen peroxide so as to form free radicals, said activation of the sterilizing agent of each sterilizing preform taking place before and/or during the step for transformation of said sterilizing preform into a hollow body by stretch blow molding.

In the above embodiment, the activation of the hydrogen peroxide makes it possible to deliver extremely germicidal free radicals directly to the stretching means. This imparts an efficiency of destruction of the microorganisms that is quite adequate despite the small amount of sterilizing agent introduced into the blow-molding machine. In fact, the germicidal power of the activated hydrogen peroxide is not proportionate with that obtained with a liquid sterilizing agent, particularly a disinfection with alcohol.

The sterilizing method according to the invention can be implemented in an existing installation by using an existing decontamination device but for sterilizing the stretching means with the sterilizing agent introduced into at least one sterilizing preform during the operating mode, so-called sterilizing mode, of the installation.

Advantageously, the batch of hollow bodies removed after sterilization of the stretching means is eliminated and recycled.

According to other characteristics of the invention that can be used separately or in combination:
  the method comprises a step for thermal conditioning of the production preforms and of the sterilizing preforms, the step for introducing an amount of sterilizing agent taking place before and/or during the step for thermal conditioning of the sterilizing preforms,
  the method comprises a step consisting in removing from the installation, on completion of the transformation step, the hollow bodies obtained from the sterilizing preforms. This makes it possible to separate clearly the sterilizing mode from the production mode. The removal makes it possible to reduce, and even eliminate, the risk of recontamination of the blow-molding machine, or of the machines for subsequent treatment of the containers.
  the transformation step consists in obtaining a partially formed container;
  the transformation step consists in obtaining a fully formed container;
  said steps of the method of sterilizing the stretching means are implemented in an operating mode of the installation, the so-called sterilizing mode, in which the molding device manufactures a series of hollow bodies;

the stretching means are kept inside the sterilizing preform that has the sterilizing agent for a predetermined period that is greater than or equal to that of a production preform;

said predetermined period of contact of the stretching means with the sterilizing agent contained inside the sterilizing preform is obtained by selectively controlling the actuating means that control the movement of said stretching means;

said predetermined period of contact of the stretching means with the sterilizing agent contained inside the sterilizing preform is obtained by acting on a rotation drive speed of a carousel of a molding machine of the manufacturing installation having the container molding device;

said sterilizing agent introduced into a sterilizing preform is the same sterilizing agent as that used for a production preform;

the determined amount of sterilizing agent introduced into the sterilizing preform is greater than or equal to that introduced into a production preform;

said sterilizing agent introduced into the sterilizing preform has physicochemical parameters that are different from the sterilizing agent introduced into a production preform;

said sterilizing agent introduced into the sterilizing preform has a concentration that is greater than that introduced into a production preform;

the sterilizing preform is heated, before the step for transformation into a hollow body, to a predetermined temperature that is different from that of a production preform;

the sterilizing preform is molded by stretch blow molding using a blow-molding fluid having a maximum pressure that is less than or equal to that of the final pressure for blow molding of a production preform;

the sterilizing preform is identical to a production preform.

According to another aspect, the invention also relates to an installation for manufacturing containers made of thermoplastic material, for implementing the above-mentioned method, having a sterilizing mode and a production mode, the installation comprising:

a molding machine equipped with at least one molding device having stretching means, the molding device being designed to manufacture by stretch blow molding said containers from production preforms when the installation is in production mode, transfer means for conveying, when the installation is in production mode, said manufactured containers between the molding machine and another machine located downstream, a decontamination device, actuated at least when the installation is in sterilizing mode, and designed for introducing the sterilizing agent into at least one sterilizing preform, the molding machine transforming the sterilizing preform into a hollow body stretched by said stretching means.

Advantageously, the installation comprises removal means that can be actuated in sterilizing mode for removing the hollow bodies from the transfer means upstream from said other machine.

According to other characteristics of the invention that can be used separately or in combination:

the installation comprises an oven for thermal conditioning of the production preforms and/or of the sterilizing preforms, the decontamination device being placed upstream, inside of or downstream from the thermal conditioning oven.

the decontamination device is designed for introducing the sterilizing agent as vapor into a sterilizing preform having a temperature that makes it possible to obtain a deposit by condensation of a uniform film of mist on an inner surface of said sterilizing preform.

the sterilizing mode initiates the successive transformation into hollow bodies of at least two sterilizing preforms in the same molding device.

the installation comprises a means for collecting the hollow bodies removed in sterilizing mode.

the installation comprises at least three container treatment machines connected to each other by conveying devices conveying each container individually so that, when the installation is in production mode, the treatment machines treat each container of a series of containers one after the other; said molding machine being a first container treatment machine, said other machine being a second container treatment machine directly connected downstream from the first treatment machine by said transfer means, and a sealing device designed for aseptically sealing off the inside of a container in relation to the outside environment constituting a third treatment machine.

Other characteristics and advantages of the invention will emerge from reading the following description for the understanding of which reference will be made to the single FIGURE illustrating the steps of the method for sterilizing the stretching means according to the invention.

Figure 1:
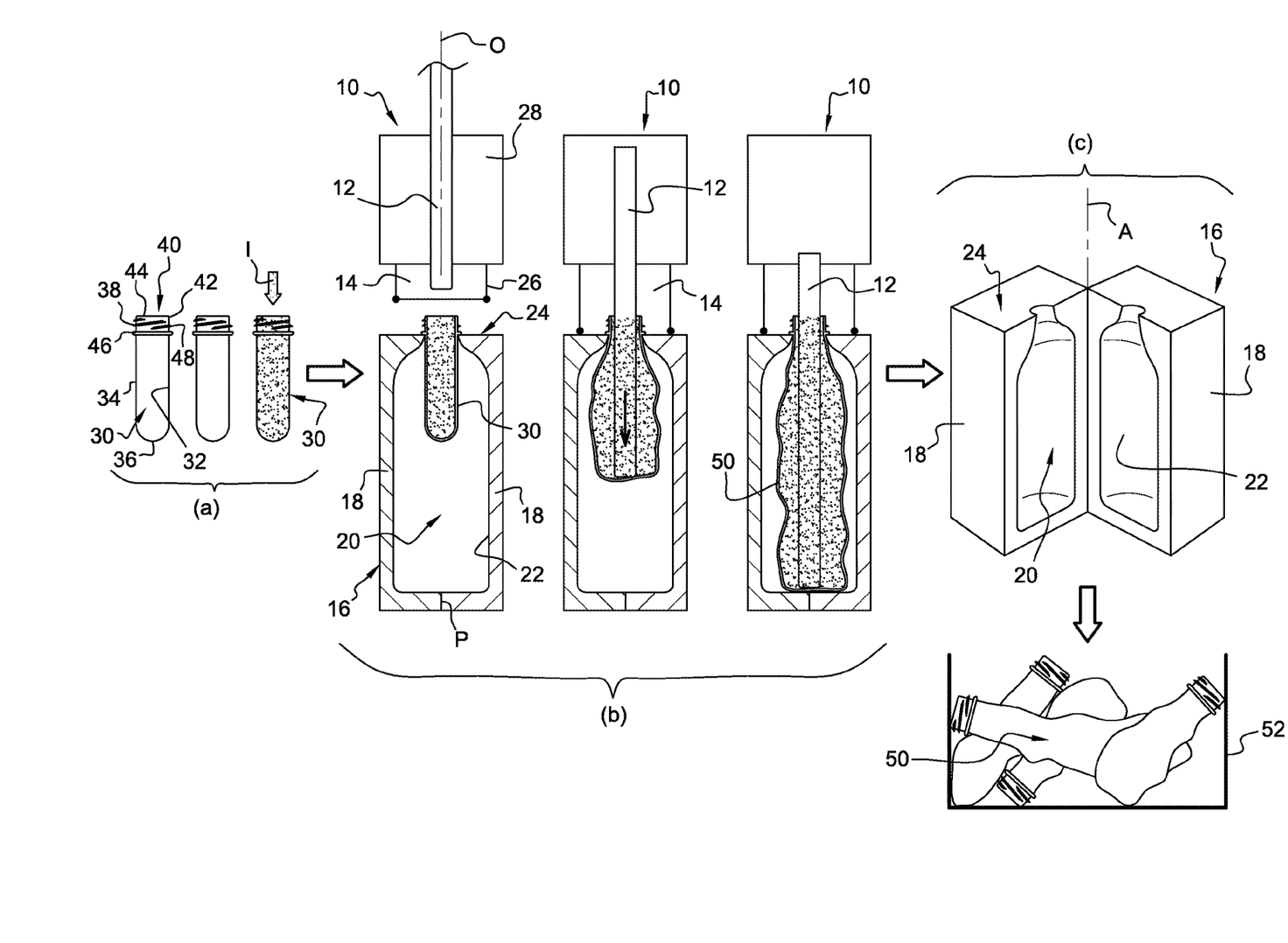

Shown diagrammatically in the single FIGURE is the implementation of the steps of the method of sterilizing the stretching means of a molding device 10 for containers made of thermoplastic material that are obtained by stretch blow molding from production preforms.

DETAILED DESCRIPTION OF THE INVENTION

According to the embodiment illustrated in the FIGURE, the molding device 10 shown is particularly able to manufacture—by stretch blow molding—containers made of thermoplastic material from production preforms.

Such a manufacture of containers corresponds to an operating mode, the so-called production mode, of the installation in which the molding device 10 is used to manufacture containers from production preforms.

The containers made of thermoplastic material manufactured as a result of such a molding device 10 are, for example, bottles, vials, or jars, particularly but not exclusively intended for the food industry.

The molding device 10 according to the embodiment shown in the FIGURE will be described below.

The molding device 10 has at least stretching means 12 and blow-molding means 14.

The molding device 10 has a mold 16 having at least two half-molds 18 that are mounted to move between at least an open position and a closed position.

The stretching means 12 and the blow-molding means 14 are arranged axially above the mold 16.

In the embodiment, the molding device 10 is a molding device of the "book like opening" type.

The molding device 10 has at least two half-molds 18 that are mounted to move around a common axis A of rotation, respectively between said open and closed positions.

The movement of opening or closing of the two half-molds 18, respectively between said open and closed positions, is controlled by, for example, mechanical means of the roller and cam type. The opening or closing movement of the half-molds 18 is particularly a function of their angular position.

In a variant, the opening or closing movement of the half-molds 18 is controlled by electric means such as electric motors positioned on the axis of the mold. The control of the opening or the closing of the half-molds 18 is therefore able to be controlled independently of the angular position of the mold of the molding device.

Such a molding device 10 generally equips a molding machine or "blowing machine" of the rotating type (not shown).

Preferably, such a molding machine has molding devices 10 that are distributed uniformly on the periphery of a carousel; said carousel is driven in rotation around a central axis.

In a variant, it is also known to use for the manufacture of containers a molding device 10 whose half-molds 18 are mounted to move in translation between at least an open position and a closed position.

The half-molds 18 together delimit a molding cavity 20 when, in the closed position, said half-molds 18 are joined along a junction plane P. The molding cavity 20 is delimited by a molding impression 22 that comprises each half-mold 18 and that corresponds in hollow form to the container to be manufactured.

In a variant, not shown, the mold 16 is made in three parts, or two half-molds 18 and a mold bottom that has an impression corresponding to the bottom of the container to be manufactured, for example a petaloid-shaped bottom.

The blow-molding means 14 are mounted to move axially between at least a raised position and a lowered position in which said blow-molding means 14 work in an airtight manner with an upper face 24 of the mold 16 that occupies the closed position.

The blow-molding means 14 have in particular sealing means 26 intended to work with said upper face 24 of the mold 16 when at least a pressurized fluid, generally air, is introduced by the blow-molding means 14 inside a production preform to manufacture the container by stretch blow molding.

Such blow-molding means 14 are known from the state of the art and consequently will not be described in further detail. By way of nonlimiting examples, however, reference can be made to the documents FR-2,764,544 or FR-2,912,678.

In the embodiment illustrated in the FIGURE, the stretching means 12 consist of a rod.

The stretching means 12 are mounted to move axially along an axis O, or between at least a retracted position and an in-use position in which said stretching means 12 are able to perform a stretching.

The molding device 10 has means 28 for actuating the stretching means 12 that are controlled to move said stretching means 12 axially between at least said retracted and in-use positions.

Preferably, the actuating means 28 are formed by an electric motor that makes it possible selectively to control the axial movement of the stretching means 12.

In a variant, the actuating means 28 consist of mechanical means of the roller and cam type that control the axial movement of the stretching means 12 as a function particularly of the angular position of the molding device 10 when said molding device 10 is moved in rotation with the carousel of a molding machine.

The production preforms are generally obtained by injection molding of thermoplastic material such as PET (Poly-Ethylene Terephthalate).

Such previously-manufactured preforms must subsequently be thermally conditioned to soften their constituent material and to make possible their transformation into containers by blow molding or by stretch blow molding.

In a variant, it is also known to transform a production preform obtained by extrusion directly into a container, such a container manufacturing method generally being called "extrusion blow molding."

Either way, the container is obtained from a hot production preform that undergoes stretching and blow-molding operations in the cavity 20 of the mold 16 of the molding device 10 in the closed position.

The molding machine (or "blowing machine") having at least one container molding device 10 generally constitutes one of the units of an installation (not shown) for manufacturing containers.

A container manufacturing installation has, for example, at least one oven for the thermal conditioning of the production preforms. The thermal conditioning oven constitutes another unit of the installation.

The installation has transfer means, such as wheels provided sometimes with grips, arranged between the different units to convey preforms or containers, for example to convey production preforms from the output of the oven to the molding machine located downstream.

Transfer means are also used in the installation to convey the manufactured containers between the molding machine and at least one other machine located downstream, such as a filling machine, a sealing machine, etc.

Advantageously, the transfer means of the installation are particularly synchronized with each other automatically and can be desynchronized on demand, which, in certain cases, proves particularly useful when the installations are rotary: it is in fact possible, by combining said transfer means with a computerized control of the opening of the molds, to prolong the time of holding the hollow body in the mold by making the hollow body stay beyond one revolution of the carousel while keeping the stretching means in the position of stretching the preforms. In other words, the removal of the hollow bodies can be delayed.

According to the applications, the installation has a decontamination device (not shown) for sterilizing at least the interior of the production preforms intended to be transformed into containers or to obtain sterile containers.

The installation can further have, downstream from the molding machine, another unit having at least a filling machine in which the filling of the manufactured containers is performed.

Preferably, also performed in such a unit is at least the closing of said containers after their filling, the closing being performed by, for example, sealing.

As explained in the preamble of the description, it is time and again sought to improve the quality of the manufacture of containers by addressing the microbial contamination risks by pathogens.

The invention has as its object to further reduce these risks of contamination by performing a sterilizing of the stretching means 12 of a molding device 10 such as the one described previously with reference to the FIGURE.

The stretching means to be sterilized according to the method are the stretching means 12 of a container molding device 10 equipping an installation for manufacturing containers made of thermoplastic material that are obtained by stretch blow molding from production preforms.

Such a previously-described installation is, for example, shown in FIG. 5 of the document WO-99/03667 or else in FIGS. 1 and 4 of the documents WO-2006/136498 and WO-2006/136499.

In the embodiment, the molding device 10 equips more specifically a molding machine (or blowing machine), said molding machine forming one of the units of the installation for manufacturing containers made of thermoplastic material.

In accordance with the invention, the method of sterilizing the stretching means 12 of a container molding device 10, equipping an installation for manufacturing containers made of thermoplastic material by stretch blow molding of production preforms, has at least the steps consisting in:
  introducing a determined amount of a sterilizing agent inside a sterilizing preform 30,
  during a so-called transformation step, transforming said sterilizing preform 30 into a hollow body 50 by stretch blow molding in said molding device 10, and
  removing from the installation, upon completion of the transformation step, the hollow body 50 obtained during this step from the sterilizing preform 30.

The steps of the method of sterilizing the stretching means 12 are implemented in an operating mode of the installation, the so-called sterilizing mode, in which the molding device 10 manufactures a series of hollow bodies from the sterilizing preforms 30.

Advantageously, the method of sterilizing the stretching means 12 is at least implemented before performing a manufacturing of containers from production preforms.

Preferably, the steps of the method of sterilizing the stretching means 12 are performed during a start-up phase of the installation preparatory to the manufacture of containers.

In the installation, the operating mode, the so-called sterilizing mode, is used prior to the other operating mode, the so-called production mode, during which containers are manufactured by at least one molding device 10 from production preforms.

In the sterilizing mode, sterilizing preforms 30 are used that are intended to be transformed into hollow bodies, while in the production mode, production preforms are used that are intended to be transformed into containers.

In the embodiment and as shown in the FIGURE, the sterilizing preform 30 is advantageously identical to a production preform.

The sterilizing preform 30 has an inner surface 32 delimited by a body 34 that is closed at one end by a bottom 36 and that, at the other end, has a neck 38 delimiting an opening 40 for access to the inside of the preform 30.

The neck 38 of the sterilizing preform 30 has its final shape on completion of its manufacture accomplished preferably by injection molding.

The sterilizing preform 30 being identical to a production preform, the neck 38 of the sterilizing preform 30 has a thread 42 that normally is intended to make possible the closing of the final container by a cap having a complementary screwthread.

The opening 40 is delimited by a rim 44 (or lip) of the neck 38, said opening 40 constituting the only access to the interior of the preform 30 since the body 34 is closed axially at the other end by the bottom 36.

In the example shown in the FIGURE, the neck 38 has a flange 46 that extends radially protruding outward. The neck 38 further has an annular groove 48 here that is adjacent to said flange 46.

However, it must be clearly understood that the sterilizing preform 30 could also be different from a production preform intended for the manufacture of a container.

In fact, the production preform has characteristics (dimensions, distribution of material, etc.) that are determined as a function of the final container to be obtained, in particular its shape or even its capacity.

By comparison, the sterilizing preform 30 is only intended to sterilize the stretching means 12 by means of the sterilizing agent that is introduced there during the first step of the sterilizing method according to the invention.

Compared with a manufacturing preform, the sterilizing preform 30 is intended to be transformed into a hollow body 50 that is removed from the installation after the sterilizing of the stretching means 12.

A sterilizing preform 30 could thus have a different neck 38, said neck 38 not having in particular thread 42 and/or groove 48 since the hollow body 50 is removed from the installation after its extraction from the molding device 10.

The hollow body 50 obtained from the sterilizing preform 30 is removed upstream from the filling unit when the installation has such a unit. Unlike the container, the hollow body 50 is in fact not intended to be filled, nor closed by sealing, for example, by means of a screw cap.

In addition to the neck 38, the sterilizing preform 30 could also be distinguished from a production preform by its weight.

Preferably, the sterilizing preform 30 is thus lighter than a production preform in order to achieve cost savings relative to the amount of thermoplastic material.

The sterilizing preform 30 has less thermoplastic material, for example a body 34 of less thickness, since the goal is not to obtain a container but to sterilize the stretching means 12.

In the example illustrated by the FIGURE, the hollow body 50 obtained at the completion of the step for transforming the sterilizing preform 30 into a hollow body 50 consists of a partially formed container.

In a variant, not shown, the hollow body 50 is a container. When the sterilizing preform 30 is identical to a production preform, the hollow body 50 is able to be identical to a container obtained by molding from a production preform.

By comparison, it will, however, be understood that a hollow body 50 consisting of a partially formed container makes it possible to achieve certain savings, particularly by using less air for the blow molding of the sterilizing preform 30.

Advantageously, the hollow body 50 consisting of a partially formed container has a smaller volume than a container with the result that the sterilizing of the stretching means 12 by the sterilizing agent present inside the sterilizing preform 30 is facilitated.

The method of sterilizing the stretching means 12 according to the invention advantageously replaces the disinfection with alcohol of the stretching means 12 performed previously manually by at least one operator before the manufacture of containers in the installation.

Compared with disinfection with alcohol, the sterilizing method makes it possible to obtain degrees of decontamination that are much higher and that can, for example, reach "6-log" depending on the sterilizing agent used.

Preferably, the sterilizing agent is hydrogen peroxide ($H_2O_2$). In a variant, the sterilizing agent, for example, consists of sodium hydroxide (NaOH).

It is recalled that the amount of microorganisms can be computed by counting particularly after washing, filtering and culturing operations. A logarithmic reduction of the number of microorganisms is thus found, for example, on the order of 3-log (or else 3D) equivalent to 1000 units ($10^3$).

Advantageously, the sterilizing method according to the invention is implemented automatically in the container manufacturing installation when the installation is in operating mode, the so-called sterilizing mode.

Compared with alcohol disinfection, the sterilizing method no longer requires the intervention of an operator inside the installation delimited by its enclosure, whereby the risks of contamination of the manufacturing environment associated with the presence of the operator are eliminated.

The chemical sterilization of the stretching means 12 by means of a sterilizing agent, such as hydrogen peroxide ($H_2O_2$), makes it possible at the very least to reduce, indeed eliminate, the pathogens that may be present on the stretching means 12 of the molding device 10.

Using the sterilization according to the invention, the risks of contamination resulting from the contact of the stretching means 12 with the inside of the production preforms from which the containers are manufactured by the molding device 10 are eliminated.

As illustrated in the FIGURE, the method of sterilizing the stretching means 12 has at least one step (a) consisting in introducing a determined amount of a sterilizing agent inside a sterilizing preform 30.

Shown diagrammatically by an arrow referenced "I" is the introduction of the determined amount of sterilizing agent inside the sterilizing preform 30.

In the FIGURE, the presence of sterilizing agent in the sterilizing preform 30 and then the hollow body 50 has been marked by dots whose choice addresses a simple convention without reference to any state in particular of the sterilizing agent.

Preferably, the introduction of the sterilizing agent according to step (a) is performed in a stream of sterilizing preforms 30, for example successively in several sterilizing preforms 30 shown in the FIGURE. In fact, to attain the degree of sterilization required, it can be necessary to apply the sterilizing method on several successive sterilizing preforms, so as to obtain the germicidal effect required for the stretching means 12.

The sterilizing agent introduced into the sterilizing preform 30 or preforms 30 can be in the liquid and/or gaseous state, particularly in the vapor state.

When the installation is in operating mode, so-called production mode, and has a device for decontamination of preforms (not shown), the decontamination device equipping it is used to introduce a sterilizing agent inside the production preforms.

In the sterilizing mode of the installation, the sterilizing agent is preferably introduced into a sterilizing preform 30 by this same decontamination device that the installation has.

Advantageously, said sterilizing agent introduced into a sterilizing preform 30 is the same sterilizing agent as the one used for a production preform.

Depending on the type of decontamination device, the sterilizing agent is introduced into a sterilizing preform 30 that is termed "cold" or "hot."

By "cold" sterilizing preform 30 is meant in particular a preform at ambient temperature into which the sterilizing agent is introduced before proceeding with the thermal conditioning of the sterilizing preform 30 in an oven.

The thermal conditioning of a sterilizing preform 30 is in particular intended to make it possible to stretch the sterilizing preform 30 axially with the stretching means 12 of the molding device 10 during a so-called transformation step (b), which will be described later.

The thermal conditioning of the sterilizing preform 30 also has the effect of thermally activating the previously-introduced sterilizing agent.

According to a first embodiment of step (a), the sterilizing agent is introduced in the liquid state inside the cold sterilizing preform 30, and the sterilizing preform 30 is then heated.

In the case of a sterilizing agent formed by hydrogen peroxide ($H_2O_2$), the heating performed will thermally activate the agent and make it possible to obtain the sterilizing effect.

Preferably, the heating is performed by radiation in a thermal conditioning oven. In a variant, the heating is performed with hot air or any other equivalent means making it possible to raise the temperature of the preform.

Preferably, the sterilizing agent in the liquid state is atomized inside the sterilizing preform 30. In a variant, the sterilizing preform 30 is filled with sterilizing agent in the liquid state and then emptied.

The implementation of the method of sterilizing the stretching means 12 according to this first example is particularly able to be carried out with a decontamination device according to the teachings of the above-cited document WO-99/03667.

In such an example, the sterilizing of the stretching means 12 is obtained during the transformation step (b) when said stretching means 12 come into contact with the sterilizing agent present inside the sterilizing preform 30.

The sterilizing agent present inside the sterilizing preform 30 is particularly in the gaseous state following the heating that causes the evaporation of all or part of the sterilizing agent.

According to a second embodiment of step (a), the sterilizing agent is introduced into a "cold" sterilizing preform 30 in the vapor state so as to obtain depositing by condensation of a uniform film of mist on the inner surface 32 of said preform 30.

The sterilizing preform 30 is then heated by radiation in an oven of the installation.

The implementation of the method of sterilizing the stretching means 12 can be performed with a decontamination device according to the technical teachings of the above-cited documents WO-2006/136498 or WO-2006/136499.

By "hot" sterilizing preform 30 is meant in particular a hot preform having a determined temperature that results from a heating, in a variant of its manufacture by extrusion, and into which the sterilizing agent is introduced.

Such a hot preform is obtained, for example, after having undertaken the thermal conditioning of the sterilizing preform 30 in an oven to make possible its axial stretching by the stretching means 12 of the molding device 10 during the transformation step (b) that will be described in further detail below.

According to a third embodiment of step (a), the sterilizing agent is introduced in the gaseous state inside a sterilizing preform 30 that is hot.

Preferably, the introduction of the sterilizing agent is performed during the transfer of the sterilizing preforms 30 between the conditioning oven of the installation and the molding machine having at least one molding device 10 provided with stretching means 12.

As is clear from the three embodiments just described, step (a) is advantageously implemented with the decontamination device of the container manufacturing installation that has the molding device 10.

Such a decontamination device is then used in the sterilizing mode of the installation to carry out step (a), which constitutes a new use of it in a particular operating mode.

In fact, the decontamination device was previously exclusively used in the production mode of the installation and for decontaminating the interior of production preforms intended to be transformed into containers.

In a variant, the determined amount of sterilizing agent is introduced into the sterilizing preform 30 during step (a) by additional means that are separate from those of the decontamination device used for decontaminating the interior of the production preforms.

The use of a decontamination device, such as, for example, one of those described in the above-cited documents for the three embodiments, is advantageously carried out with operating parameters that are determined and specific to the production operating mode of the installation having the molding device 10.

In fact, in sterilizing mode of the installation, the molding device 10 is used to obtain, from sterilizing preforms 30, a series of hollow bodies 50 that are intended to be removed from the installation after the sterilization of the stretching means 12.

Advantageously, the determined amount of sterilizing agent introduced into a sterilizing preform 30 can therefore be different from that introduced into a production preform.

Preferably, the determined amount of sterilizing agent introduced into a sterilizing preform 30 is greater than or equal to the amount of sterilizing agent introduced into a production preform.

In fact, and unlike a container, the residual amount of sterilizing agent present in a hollow body 50 is not important since the hollow body 50 is eliminated.

Advantageously, said sterilizing agent introduced into the sterilizing preform 30 has physicochemical parameters that are different from the physicochemical parameters of the sterilizing agent introduced into a production preform.

Preferably, the sterilizing agent introduced into the sterilizing preform 30 has a concentration that is higher than the concentration of the sterilizing agent introduced into a production preform.

The sterilizing preform 30 has the function of containing the sterilizing agent used for sterilizing the stretching means 12 of the molding device 10.

Preferably, the sterilizing preform 30 is heated, before the transformation step (b), to a given temperature that is different from the molding temperature of a production preform.

Preferably, the sterilizing preform 30 is heated, before the transformation step (b), to a given temperature that is greater than or equal to the molding temperature of a production preform.

Advantageously, the value of the temperature to which the sterilizing preform 30 is heated is determined as a function of the determined amount of sterilizing agent introduced before the heating inside the sterilizing preform 30.

The value of the temperature is then particularly determined to obtain the thermal activation of the sterilizing agent, the change in state by evaporation of all or part of the sterilizing agent [sic].

In a variant, the sterilizing preform 30 is heated, before the transformation step (b), to a given temperature that is less than or equal to the molding temperature of a production preform.

The value of the temperature is thus particularly determined to make possible, during said step (b), the axial stretching of the sterilizing preform 30 by the sterilized stretching means 12.

The sterilizing preform 30 is intended for the sterilizing of the stretching means 12. Also, compared with a production preform, the obtaining of a well-formed container is not necessarily sought during the transformation step.

This is why the hollow body 50 obtained by stretch blow molding from the sterilizing preform 30 can in particular be a partially formed container, such as an intermediate container, as is illustrated in the FIGURE.

As illustrated in the FIGURE and indicated previously, the method of sterilizing the stretching means 12 according to the invention has a step (b) consisting in transforming said sterilizing preform 30 into a hollow body 50 by stretch blow molding in said molding device 10.

After step (a) during which the sterilizing agent is introduced inside a hot sterilizing preform 30, said sterilizing preform 30 is transferred to the molding device 10.

The sterilizing preform 30 containing the sterilizing agent (marked by dots) is introduced into the mold 16 of the molding device 10 in the open position; the half-molds 18 of the mold 16 are then moved to the closed position.

As illustrated in the first view (on the left) of the FIGURE for step (b), the sterilizing preform 30 is held in the mold 16 in the closed position by means of its flange 46 that rests on the upper face 24.

The sterilizing preform 30 extends axially through an opening of the mold 16 made in the upper face 24, the neck 38 of the preform 30 extending protruding out of the mold 16 and the body 34 extending inside of the molding cavity 20.

As illustrated in the first view (on the left) of the FIGURE for step (b), the stretching means 12 are in retracted position and the blow-molding means 14 in the raised position.

Then and as illustrated in the second view (in the center) of the FIGURE for step (b), the blow-molding means 14 are moved axially from the raised position to the lowered position in which the sealing means 26 work with the upper face 24 of the mold 16.

The blow-molding means 14 initiate the introduction of at least one blow-molding fluid, such as pressurized air, inside the sterilizing preform 30 to carry out the transformation step by stretch blow molding of the sterilizing preform 30 at the completion of which the hollow body 50 is obtained.

Advantageously, the sterilizing preform 30 is transformed by stretch blow molding by means of a blow-molding fluid having a maximum pressure that is different from the final blow-molding pressure of a production preform.

Preferably, the sterilizing preform 30 is transformed by stretch blow molding by means of a blow-molding fluid having a maximum pressure that is less than the final blow-molding pressure of a production preform.

This is why the hollow body 50 obtained and illustrated in the third view (on the right) of the FIGURE for step (b) can be a partially formed container.

In a variant, not shown, the sterilizing preform 30 is transformed by stretch blow molding by means of a blow-molding fluid having a maximum pressure that is equal to the final blow-molding pressure of a production preform.

In such a variant, the hollow body 50 obtained from the sterilizing preform 30 is able to be completely molded and to constitute a container having the shape of the molding cavity 20.

In addition to the blow-molding means 14, the stretching means 12 are also moved axially from the retracted position to the in-use position along the arrow shown on the stretching means 12 and directed downward.

The stretching means 12 then penetrate inside the sterilizing preform 30 and come into contact with the bottom 36 of it to perform an axial stretching of said preform 30.

As illustrated in the third view (on the right) of the FIGURE for step (b), the stretching means 12 continue their descent inside the molding cavity 20 until axially reaching the bottom of the mold 16.

Compared with the first view, the third view represents the hollow body 50 obtained at the completion of the transformation step by stretch blow molding from the sterilizing preform 30.

During the transformation step (b), the stretching means 12 are sterilized by the sterilizing agent present initially inside the sterilizing preform 30.

Advantageously, during the transformation step (b), the stretching means 12 are kept inside the sterilizing preform 30 having the sterilizing agent for a given period that is the period corresponding to the stretching of a production preform during the manufacture of a container.

The purpose of the stretching of the sterilizing preform 30 during step (b) is in fact to sterilize the stretching means 12 by putting them into contact with the sterilizing agent.

In the sterilizing mode of the installation, the goal is not to manufacture a container as during the production mode.

This is why the parameters related to the stretching means 12, such as the speed of axial movement, etc., are determined to obtain their sterilization (and not necessarily for obtaining a container).

Advantageously, the stretching means 12 are kept inside the sterilizing preform 30 having the sterilizing agent and then the hollow body 50 that is obtained for a given period that is greater than or equal to the stretching period of a production preform for manufacturing a container.

Preferably, the given period of contact of the stretching means 12 with the sterilizing agent contained inside the sterilizing preform 30 is obtained by selectively controlling the actuating means 28 that control the movement of said stretching means 12.

The modification of the parameters for control of the stretching means 12 will be preferred in particular when the actuating means 28 consist of at least one electric motor.

In a variant, the given period of contact of the stretching means 12 with the sterilizing agent contained inside the sterilizing preform 30 is obtained by acting on the speed of driving in rotation of the carousel of the molding machine of the manufacturing installation having said at least one molding device 10.

Such a variant will be preferred in particular when the means 28 for operating the stretching means 12 are mechanical means of the roller and cam type.

During the transformation step (b), the stretching means 12 can be moved axially in translation and/or in rotation, during and/or after the transformation of the sterilizing preform 30 into a hollow body 50.

Once the transformation step (b) of the sterilizing preform 30 is completed, the stretching means 12 are moved axially by the actuating means 28 from the in-use position to the initial retracted position, i.e., upward as illustrated in the FIGURE.

The blow-molding means 14 are also moved axially, raised from the low position to the high position.

The stretching means 12 and the blow-molding means 14 thus respectively occupy the same position as that illustrated in the first view on the left of step (b).

The mold 16 of the molding device 10 in the closed position has inside the molding cavity 20 the hollow body 50 obtained from said sterilizing preform 30.

As illustrated in the FIGURE, the method of sterilizing the stretching means 12 has a step (c) consisting in removing from the installation, on completion of the transformation step, the hollow body (50) obtained during this step from the sterilizing preform (30).

In one implementation, when the opening of the molds can be controlled independently from their angular position in relation to a frame of a machine (in the case of rotary machines), the half-molds 18 are kept in the closed position past their transition to the open position during production phases, the blow-molding means 14 remaining in low position and the stretching means 12 remaining in in-use position or moved at least axially in translation between said retracted and in-use positions, and even also in rotation. Therefore, the contact time between the stretching means 12 and the sterilizing agent is significantly increased (typically over more than one carousel rotation).

For the removal step (c), the opening of the mold 16 of the molding device 10 is initiated to extract said hollow body 50 from the molding cavity 20.

Preferably, the hollow body 50 is removed toward collection means 52 such as a bin shown in the FIGURE.

The removal of the hollow body 50 is advantageously carried out directly after its extraction from the mold 16 of the molding device 10.

In an installation comprising a filling unit, the removal of the hollow bodies 50 is carried out upstream from such a filling unit.

When the installation has closing means, such as a sliding door, making it possible to seal off the filling unit in relation to the filling machine, said closing means are then controlled to occupy their closed position, and the removal takes place upstream from this door.

The above-cited document FR-2,940,964 describes, for example, an installation having such closing means formed by a door.

The collection means 52 are intended to recover the series of hollow bodies 50 manufactured from sterilizing preforms 30 during the implementation of the method of sterilizing the stretching means 12 in the so-called sterilizing operating mode of the installation.

Advantageously, said series of hollow bodies 50 removed from the installation during step (c) is eliminated.

Preferably, the series of hollow bodies 50 is eliminated by grinding to be transformed into a ground material of thermoplastic.

Advantageously, the ground material obtained is processed so as to eliminate the sterilizing agent that can be present and to make possible a recycling of the thermoplastic material.

The thermoplastic material is, for example, recycled to manufacture preforms by injection molding or by extrusion molding.

The invention claimed is:

1. An installation for manufacturing containers made of thermoplastic material, the installation comprising a sterilizing mode and a production mode, the installation comprising:
   a molding machine equipped with at least one molding device having stretching means, the molding device being designed to manufacture by stretch blow molding said containers from preforms when the installation is in production mode;

a transfer wheel for conveying, when the installation is in production mode, said manufactured containers between the molding machine and a second machine located downstream;

a decontamination device for use in sterilizing mode and designed for introducing a sterilizing agent into at least one preform, the molding machine transforming the preform into a hollow body that is at least partially stretched by said stretching means;

at least one computerized control to prolong the time of holding the at least partially stretched hollow body within a mold of the molding machine; and a removal actuator that operates in the sterilizing mode to remove the at least partially stretched hollow body from the transfer wheel upstream from the second machine, thereby eliminating any risks of the of the at least partially stretched hollow body contaminates the second machine, wherein the transfer wheel is desynchronized from the second machine during use of the removal actuator.

2. The installation of claim 1, further comprising a containment bin for collecting the at least partially stretched hollow body removed from the transfer wheel in sterilizing mode.

3. The installation of claim 1, wherein the stretching means comprises at least a stretching rod, and wherein the stretching rod is sterilized when being used to stretch the sterilizing preform into the hollow body.

4. The installation of claim 3, wherein the stretching rod remains at least partially extended and within the hollow body of the sterilizing preform for a predetermined amount of time so as to expose the stretching means to the sterilizing agent.

5. The installation according to claim 1, further comprising an oven for thermal conditioning of the preforms, the decontamination device being placed upstream, inside of or downstream from the thermal conditioning oven.

6. The installation according to claim 1, wherein the decontamination device is designed for introducing the sterilizing agent in the vapor state into the preform having a temperature that makes it possible to obtain a deposit by condensation of a uniform film of mist on an inner surface of said sterilizing preform.

7. The installation according to claim 1, wherein the sterilizing mode initiates the successive transformation into partially formed hollow bodies of at least two sterilizing preforms in the same molding device.

8. The installation according to claim 1, further comprising at least three container treatment machines connected to each other by conveying devices conveying each container individually so that, when the installation is in production mode, the treatment machines treat each container of a series of containers one after the other; said molding machine being a first container treatment machine, said other machine being a second container treatment machine directly connected downstream from the first treatment machine by said transfer wheel, and a sealing device designed for aseptically sealing off the inside of a container in relation to the outside environment constituting a third treatment machine.

9. An installation for manufacturing containers made of thermoplastic material, the installation comprising a sterilizing mode and a production mode, the installation comprising:

a molding machine equipped with at least one molding device having a mold, blow-molding means, and stretching means, the molding device being designed to manufacture by stretch blow molding said containers from production preforms when the installation is in production mode;

a transfer wheel for conveying, when the installation is in production mode, said manufactured containers between the molding machine and a second machine located downstream;

a decontamination device for use in sterilizing mode and designed for introducing a sterilizing agent into at least one sterilizing preform, the molding machine transforming the sterilizing preform into a hollow body that is at least partially stretched by said stretching means; and a removal actuator that operates in the sterilizing mode to remove the at least partially stretched hollow body from the transfer wheel upstream from the second machine, the transfer wheel being desynchronized from the second machine during use of the removal actuator, wherein in sterilizing mode, the at least partially stretched hollow body of the sterilizing preform remains within the mold of the at least one molding device for a first period of time and in production mode the container that is stretched by the production preform remains within the mold of the at least one molding device for a second period of time, and wherein the first period of time is greater than the second period of time.

10. The installation of claim 9, further comprising a containment bin for collecting the at least partially stretched hollow body removed from the transfer wheel in sterilizing mode.

11. The installation of claim 9, wherein the stretching means comprises at least a stretching rod, and wherein the stretching rod is sterilized when being used to stretch the sterilizing preform into the hollow body.

12. The installation of claim 10, wherein the stretching rod remains at least partially extended and within the hollow body of the sterilizing preform for a predetermined amount of time so as to expose the stretching means to the sterilizing agent.

13. The installation according to claim 9, further comprising an oven for thermal conditioning of the preforms, the decontamination device being placed upstream, inside of or downstream from the thermal conditioning oven.

14. The installation according to claim 9, wherein the decontamination device is designed for introducing the sterilizing agent in the vapor state into the preform having a temperature that makes it possible to obtain a deposit by condensation of a uniform film of mist on an inner surface of said sterilizing preform.

15. The installation according to claim 9, wherein the sterilizing mode initiates the successive transformation into partially formed hollow bodies of at least two sterilizing preforms in the same molding device.

16. The installation according to claim 9, further comprising at least three container treatment machines connected to each other by conveying devices conveying each container individually so that, when the installation is in production mode, the treatment machines treat each container of a series of containers one after the other; said molding machine being a first container treatment machine, said other machine being a second container treatment machine directly connected downstream from the first treatment machine by said transfer wheel, and a sealing device designed for aseptically sealing off the inside of a container in relation to the outside environment constituting a third treatment machine.

17. An installation for manufacturing containers made of thermoplastic material, the installation comprising a sterilizing mode and a production mode, the installation comprising:
- a molding machine equipped with at least one molding device having stretching means, the molding device being designed to manufacture by stretch blow molding said containers from preforms when the installation is in production mode;
- a transfer wheel for conveying, when the installation is in production mode, said manufactured containers between the molding machine and a second machine located downstream;
- a decontamination device for use in sterilizing mode and designed for introducing a sterilizing agent into at least one preform, the molding machine transforming the preform into a hollow body that is at least partially stretched by said stretching means;
- at least one computerized control to prolong the time of holding the at least partially stretched hollow body within a mold of the molding machine; and
- a removal actuator that operates in the sterilizing mode to remove the at least partially stretched hollow body the transfer wheel upstream form the second machine, the transfer wheel being desynchronized from the second machine during use of the removal actuator.

18. The installation according to claim 17, wherein in sterilizing mode, the at least partially stretched hollow body of the sterilizing preform remains within the mold of the at least one molding device for a first period of time and in production mode the container that is stretched by the production preform remains within the mold of the at least one molding device for a second period of time, and wherein the first period of time is greater than the second period of time.

* * * * *